(12) United States Patent
DiMatteo et al.

(10) Patent No.: US 11,576,664 B2
(45) Date of Patent: Feb. 14, 2023

(54) METHODS FOR ANCHORING SUTURE TO BONE

(71) Applicant: DePuy Synthes Products, Inc., Raynham, MA (US)

(72) Inventors: Kristian DiMatteo, Waltham, MA (US); Chris Kilburn-Peterson, Needham, MA (US); Nathan S. Cauldwell, Attleboro, MA (US); Jonathan Howe, Mansfield, MA (US); Hugh S. West, Murray, UT (US)

(73) Assignee: DEPUY SYNTHES PRODUCTS, INC, Raynham, MA (US)

( * ) Notice: Subject to any disclaimer, the term of this patent is extended or adjusted under 35 U.S.C. 154(b) by 644 days.

(21) Appl. No.: 16/446,931

(22) Filed: Jun. 20, 2019

(65) Prior Publication Data

US 2019/0365374 A1    Dec. 5, 2019

Related U.S. Application Data

(63) Continuation of application No. 14/198,127, filed on Mar. 5, 2014, now Pat. No. 10,327,752, which is a
(Continued)

(51) Int. Cl.
*A61B 17/04* (2006.01)
*A61B 17/86* (2006.01)

(52) U.S. Cl.
CPC ........ *A61B 17/0401* (2013.01); *A61B 17/863* (2013.01); *A61B 2017/044* (2013.01); *A61B 2017/0409* (2013.01)

(58) Field of Classification Search
CPC ........ A61B 2017/044; A61B 2017/042; A61B 2017/0445; A61B 2017/0412; A61B 2017/0409; A61B 17/0401; A61B 17/863
(Continued)

(56) References Cited

U.S. PATENT DOCUMENTS 2,382,019 A    8/1945  Miller
2,453,247 A    11/1948 Moss
(Continued)

FOREIGN PATENT DOCUMENTS

EP    0464479 A1    1/1992
EP    0465910 A1    1/1992
(Continued)

OTHER PUBLICATIONS

U.S. Appl. No. 11/555,545.
(Continued)

*Primary Examiner* — Majid Jamialahmadi

(57) ABSTRACT

Methods and devices are provided for anchoring suture to bone. In one exemplary embodiment, a cannulated suture anchor is provided and it includes a suture-engaging member formed therein and configured to receive a suture therearound such that trailing ends of the suture can extend through the suture anchor. The suture anchor can also include at least a proximal portion having dual threads to facilitate engagement with bone. The present invention also provides exemplary sutures and drivers that can be used with the various methods and devices disclosed herein, or with other methods and devices known in the art.

7 Claims, 10 Drawing Sheets

Related U.S. Application Data continuation of application No. 11/855,670, filed on Sep. 14, 2007, now Pat. No. 8,882,801, and a continuation of application No. 11/855,728, filed on Sep. 14, 2007, now Pat. No. 8,702,754.

(58) Field of Classification Search
USPC ........................................................ 606/315
See application file for complete search history.

(56) References Cited

U.S. PATENT DOCUMENTS

| | | |
|---|---|---|
| 3,438,299 A | 4/1969 | Gutshall |
| 3,541,918 A | 11/1970 | Johnson |
| 3,762,418 A | 10/1973 | Wasson |
| RE28,111 E | 8/1974 | Laverty |
| 3,861,269 A | 1/1975 | Laverty |
| 4,027,573 A | 6/1977 | Laverty |
| 4,175,555 A | 11/1979 | Herbert |
| 4,241,638 A | 12/1980 | Shimizu et al. |
| 4,372,293 A | 2/1983 | Vijil-Rosales |
| 4,463,753 A | 8/1984 | Gustilo |
| 4,576,534 A | 3/1986 | Barth et al. |
| 4,632,100 A | 12/1986 | Somers et al. |
| 4,643,178 A | 2/1987 | Nastari et al. |
| 4,870,957 A | 10/1989 | Goble et al. |
| 4,946,468 A | 8/1990 | Li |
| 5,041,129 A | 8/1991 | Hayhurst et al. |
| 5,100,417 A | 3/1992 | Cerier et al. |
| 5,152,790 A | 10/1992 | Rosenberg et al. |
| 5,156,616 A | 10/1992 | Meadows et al. |
| 5,176,682 A | 1/1993 | Chow |
| 5,258,016 A | 11/1993 | DiPoto et al. |
| 5,320,629 A | 6/1994 | Noda et al. |
| 5,336,231 A | 8/1994 | Adair |
| 5,370,662 A | 12/1994 | Stone et al. |
| 5,374,278 A | 12/1994 | Chesterfield et al. |
| 5,417,712 A | 5/1995 | Whittaker et al. |
| 5,423,860 A | 6/1995 | Lizardi et al. |
| 5,443,482 A | 8/1995 | Stone |
| 5,443,509 A | 8/1995 | Boucher et al. |
| 5,454,823 A | 10/1995 | Richardson et al. |
| 5,464,427 A | 11/1995 | Curtis et al. |
| 5,470,334 A | 11/1995 | Ross et al. |
| 5,486,197 A | 1/1996 | Le et al. |
| 5,505,736 A | 4/1996 | Reimels et al. |
| 5,527,322 A | 6/1996 | Klein et al. |
| 5,534,011 A | 7/1996 | Greene, Jr. et al. |
| 5,571,139 A | 11/1996 | Jenkins, Jr. |
| 5,573,547 A | 11/1996 | LeVeen et al. |
| 5,573,548 A | 11/1996 | Nazre et al. |
| 5,575,801 A | 11/1996 | Habermeyer et al. |
| 5,584,835 A | 12/1996 | Greenfield |
| 5,593,410 A | 1/1997 | Vrespa |
| 5,601,557 A | 2/1997 | Hayhurst |
| 5,607,428 A | 3/1997 | Lin |
| 5,643,295 A | 7/1997 | Yoon |
| 5,674,230 A | 10/1997 | Tovey et al. |
| 5,702,397 A | 12/1997 | Goble et al. |
| 5,707,395 A | 1/1998 | Li |
| 5,720,766 A | 2/1998 | Zang et al. |
| 5,733,307 A | 3/1998 | Dinsdale |
| 5,779,417 A | 7/1998 | Barth et al. |
| 5,782,864 A | 7/1998 | Lizardi |
| 5,814,070 A | 9/1998 | Borzone et al. |
| 5,851,219 A | 12/1998 | Goble et al. |
| 5,868,789 A | 2/1999 | Huebner |
| 5,891,168 A | 4/1999 | Thal |
| 5,895,351 A | 4/1999 | Nottage et al. |
| 5,916,224 A | 6/1999 | Esplin |
| 5,935,129 A | 8/1999 | McDevitt et al. |
| 5,941,882 A | 8/1999 | Jammet et al. |
| 5,957,953 A | 9/1999 | DiPoto et al. |
| 5,961,524 A | 10/1999 | Crombie |
| 6,001,101 A | 12/1999 | Augagneur et al. |
| 6,027,523 A | 2/2000 | Schmieding |
| 6,045,573 A | 4/2000 | Wenstrom, Jr. et al. |
| 6,096,060 A | 8/2000 | Fitts et al. |
| 6,117,162 A | 9/2000 | Schmieding et al. |
| 6,123,711 A | 9/2000 | Winters |
| 6,129,730 A | 10/2000 | Bono et al. |
| 6,139,565 A | 10/2000 | Stone et al. |
| 6,146,406 A | 11/2000 | Shluzas et al. |
| 6,149,653 A | 11/2000 | Deslauriers |
| 6,159,235 A | 12/2000 | Kim |
| 6,214,031 B1 | 4/2001 | Schmieding et al. |
| 6,234,797 B1 | 5/2001 | Ura |
| 6,261,292 B1 | 7/2001 | Diebold et al. |
| 6,264,677 B1 | 7/2001 | Simon et al. |
| 6,319,270 B1 | 11/2001 | Grafton et al. |
| 6,432,115 B1 | 8/2002 | Mollenauer et al. |
| 6,436,100 B1 | 8/2002 | Berger |
| 6,436,124 B1 | 8/2002 | Anderson et al. |
| 6,461,373 B2 | 10/2002 | Wyman et al. |
| 6,464,706 B1 | 10/2002 | Winters |
| 6,503,251 B1 | 1/2003 | Shadduck |
| 6,508,830 B2 | 1/2003 | Steiner |
| 6,517,542 B1 | 2/2003 | Papay et al. |
| 6,554,830 B1 | 4/2003 | Chappius |
| 6,554,852 B1 | 4/2003 | Oberlander |
| 6,569,186 B1 | 5/2003 | Winters et al. |
| 6,569,188 B2 | 5/2003 | Grafton et al. |
| 6,585,730 B1 | 7/2003 | Foerster |
| 6,610,079 B1 | 8/2003 | Li et al. |
| 6,610,080 B2 | 8/2003 | Morgan |
| 6,616,665 B2 | 9/2003 | Grafton et al. |
| 6,623,492 B1 | 9/2003 | Berube et al. |
| 6,641,596 B1 | 11/2003 | Lizardi |
| 6,652,563 B2 | 11/2003 | Dreyfuss |
| 6,656,183 B2 | 12/2003 | Colleran et al. |
| 6,660,023 B2 | 12/2003 | McDevitt et al. |
| 6,685,728 B2 | 2/2004 | Sinnott et al. |
| 6,699,250 B1 | 3/2004 | Osterle et al. |
| 6,770,076 B2 | 8/2004 | Foerster |
| 6,773,440 B2 | 8/2004 | Gannoe et al. |
| 6,773,450 B2 | 8/2004 | Leung et al. |
| 6,840,953 B2 | 1/2005 | Martinek |
| 6,923,824 B2 | 8/2005 | Morgan et al. |
| 7,090,690 B2 | 8/2006 | Foerster et al. |
| 7,217,279 B2 | 5/2007 | Reese |
| 7,306,614 B2 | 12/2007 | Weller et al. |
| 7,322,978 B2 | 1/2008 | West, Jr. |
| 7,390,328 B2 | 6/2008 | Modesitt |
| 7,473,252 B2 | 1/2009 | Barry |
| 7,556,640 B2 | 7/2009 | Foerster |
| 7,695,494 B2 | 4/2010 | Foerster |
| 7,699,852 B2 | 4/2010 | Frankel et al. |
| 7,717,947 B1 | 5/2010 | Wilberg et al. |
| 8,083,769 B2 | 12/2011 | Cauldwell et al. |
| 8,114,128 B2 | 2/2012 | Cauldwell et al. |
| 8,167,906 B2 | 5/2012 | Cauldwell et al. |
| 8,394,123 B2 | 3/2013 | Cauldwell et al. |
| 8,597,328 B2 | 12/2013 | Cauldwell et al. |
| 9,271,715 B2 | 3/2016 | Cauldwell et al. |
| 10,327,752 B2 | 6/2019 | DiMatteo et al. |
| 2001/0004694 A1 | 6/2001 | Carchidi et al. |
| 2001/0021852 A1 | 9/2001 | Chappius |
| 2001/0037113 A1 | 11/2001 | Justin |
| 2001/0053913 A1 | 12/2001 | Freedland |
| 2002/0016594 A1 | 2/2002 | Schlapfer et al. |
| 2002/0052629 A1 | 5/2002 | Morgan et al. |
| 2002/0147463 A1 | 10/2002 | Martinek |
| 2002/0173822 A1 | 11/2002 | Justin et al. |
| 2002/0183751 A1 | 12/2002 | Justin et al. |
| 2003/0004545 A1 | 1/2003 | Burkhart et al. |
| 2003/0065332 A1 | 4/2003 | TenHuisen et al. |
| 2003/0065361 A1 | 4/2003 | Dreyfuss |
| 2003/0074002 A1 | 4/2003 | West |
| 2003/0083662 A1 | 5/2003 | Middleton |
| 2003/0088252 A1 | 5/2003 | Kaikkonen et al. |
| 2003/0125745 A1 | 7/2003 | Tseng et al. |
| 2003/0144696 A1 | 7/2003 | Sinnott et al. |
| 2003/0158555 A1 | 8/2003 | Sanders et al. |
| 2003/0187446 A1 | 10/2003 | Overaker et al. |
| 2003/0187477 A1 | 10/2003 | Lintner |

(56) References Cited

U.S. PATENT DOCUMENTS

| | | |
|---|---|---|
| 2003/0229350 A1 | 12/2003 | Kay |
| 2004/0006346 A1 | 1/2004 | Holmen et al. |
| 2004/0098050 A1 | 5/2004 | Foerster et al. |
| 2004/0106949 A1 | 6/2004 | Cohn et al. |
| 2004/0116963 A1 | 6/2004 | Lattouf |
| 2004/0199185 A1 | 10/2004 | Davignon |
| 2004/0225292 A1 | 11/2004 | Sasso et al. |
| 2005/0107828 A1 | 5/2005 | Reese |
| 2005/0119698 A1 | 6/2005 | Martinek |
| 2005/0222618 A1 | 10/2005 | Dreyfuss et al. |
| 2005/0222619 A1 | 10/2005 | Dreyfuss et al. |
| 2005/0267479 A1 | 12/2005 | Morgan et al. |
| 2005/0283158 A1 | 12/2005 | West |
| 2006/0079904 A1 | 4/2006 | Thal |
| 2006/0099109 A1 | 5/2006 | Olofsson et al. |
| 2006/0100630 A1* | 5/2006 | West, Jr. .............. A61B 17/863 606/232 |
| 2006/0247642 A1 | 11/2006 | Stone et al. |
| 2006/0276841 A1 | 12/2006 | Barbieri et al. |
| 2006/0282083 A1 | 12/2006 | Fanton et al. |
| 2007/0060922 A1 | 3/2007 | Dreyfuss |
| 2007/0073299 A1 | 3/2007 | Dreyfuss et al. |
| 2007/0203498 A1 | 8/2007 | Gerber et al. |
| 2007/0213730 A1 | 9/2007 | Martinek et al. |
| 2007/0219557 A1 | 9/2007 | Bourque et al. |
| 2007/0219558 A1 | 9/2007 | Deutsch |
| 2007/0225719 A1 | 9/2007 | Stone et al. |
| 2007/0233122 A1 | 10/2007 | Denis et al. |
| 2007/0282341 A1 | 12/2007 | Hes et al. |
| 2007/0288025 A1 | 12/2007 | Peukert et al. |
| 2008/0004659 A1 | 1/2008 | Burkhart et al. |
| 2008/0009904 A1 | 1/2008 | Bourque et al. |
| 2008/0147063 A1 | 6/2008 | Cauldwell et al. |
| 2008/0147064 A1 | 6/2008 | Cauldwell et al. |
| 2008/0147119 A1 | 6/2008 | Cauldwell et al. |
| 2009/0076544 A1 | 3/2009 | DiMatteo et al. |
| 2009/0076545 A1 | 3/2009 | DiMatteo et al. |
| 2010/0030135 A1 | 2/2010 | Mitchell |
| 2010/0185238 A1 | 7/2010 | Cauldwell et al. |
| 2012/0065679 A1 | 3/2012 | Cauldwell et al. |

FOREIGN PATENT DOCUMENTS

| | | |
|---|---|---|
| EP | 0673624 A2 | 9/1995 |
| EP | 1448543 A1 | 8/2004 |
| EP | 1719450 A1 | 11/2006 |
| GB | 1448543 A | 9/1976 |
| JP | 09056727 A | 3/1997 |
| JP | 2006512144 A | 4/2006 |
| WO | WO-9730649 A1 | 8/1997 |
| WO | WO-0209601 A2 | 2/2002 |
| WO | WO-03029237 A1 | 4/2003 |
| WO | WO-03070108 A1 | 8/2003 |
| WO | WO-04060173 A1 | 7/2004 |
| WO | WO-06099109 A2 | 9/2006 |
| WO | WO-07063285 A1 | 6/2007 |
| WO | WO-07095426 A1 | 8/2007 |

OTHER PUBLICATIONS

U.S. Appl. No. 11/555,557.
U.S. Appl. No. 11/555,568.
U.S. Appl. No. 11/855,670.
U.S. Appl. No. 11/855,728.
U.S. Appl. No. 12/749,109.
U.S. Appl. No. 13/299,670.
U.S. Appl. No. 13/423,696.
U.S. Appl. No. 14/198,127.
U.S. Appl. No. 14/996,548.
European Search Report issued in European Application No. 07254114.7 dated Dec. 28, 2007.
European Search Report issued in European Application No. 07254115.4 dated Apr. 11, 2008.
Partial European Search Report issued in European Application No. 08164065.8 dated Mar. 29, 2010.
European Search Report issued in European Application No. 08164065.8 dated Aug. 18, 2010.
Office Action, dated Sep. 23, 2014, U.S. Appl. No. 13/423,696.
Examiner's Requisition issued in Canadian Application No. 2,608,903 dated Mar. 8, 2010.
Indian Office Action for Application No. 1578/KOL/2008 dated Sep. 28, 2017.
Office Action issued in Chinese Application No. 200810173771.5 dated Feb. 17, 2013. (English translation).
Office Action issued in Japanese Application No. 2007-283534 dated Jul. 31, 2012.
Office Action issued in Japanese Application No. 2007-283568 dated Jun. 26, 2012.
Office Action, dated Oct. 20, 2014, U.S. Appl. No. 14/198,127.
Office Action issued in Japanese Application No. 2008-234418 dated Feb. 5, 2013.
Office Action issued in U.S. Appl. No. 11/555,545 dated Aug. 16, 2010.
Office Action issued in U.S. Appl. No. 11/555,545 dated Dec. 17, 2008.
Office Action issued in U.S. Appl. No. 11/555,545 dated Feb. 2, 2011.
Office Action issued in U.S. Appl. No. 11/555,545 dated May 10, 2011.
Office Action issued in U.S. Appl. No. 11/555,545 dated May 13, 2010.
Office Action issued in U.S. Appl. No. 11/555,545 dated May 19, 2009.
Office Action issued in U.S. Appl. No. 11/555,545 dated Oct. 5, 2009.
Office Action issued in U.S. Appl. No. 11/555,557 dated Dec. 17, 2008.
Office Action issued in U.S. Appl. No. 11/555,557 dated Dec. 22, 2009.
Office Action issued in U.S. Appl. No. 11/555,557 dated Feb. 10, 2011.
Office Action issued in U.S. Appl. No. 11/555,557 dated Jul. 23, 2009.
Office Action issued in U.S. Appl. No. 11/555,557 dated Jun. 7, 2011.
Office Action issued in U.S. Appl. No. 11/555,557 dated May 11, 2009.
Office Action issued in U.S. Appl. No. 11/555,557 dated Sep. 3, 2010.
Office Action issued in U.S. Appl. No. 11/555,568 dated Aug. 18, 2009.
Office Action issued in U.S. Appl. No. 11/555,568 dated Dec. 28, 2009.
Office Action issued in U.S. Appl. No. 11/555,568 dated Dec. 31, 2008.
Office Action issued in U.S. Appl. No. 11/555,568 dated Feb. 10, 2011.
Office Action issued in U.S. Appl. No. 11/555,568 dated Nov. 1, 2010.
Office Action issued in U.S. Appl. No. 11/855,670 dated Aug. 25, 2010.
Office Action issued in U.S. Appl. No. 11/855,670 dated Mar. 23, 2010.
Office Action issued in U.S. Appl. No. 11/855,670 dated Nov. 23, 2012.
Office Action issued in U.S. Appl. No. 11/855,728 dated Aug. 17, 2010.
Office Action issued in U.S. Appl. No. 11/855,728 dated Mar. 4, 2010.
Office Action issued in U.S. Appl. No. 11/855,728 dated Nov. 23, 2012.
Office Action issued in U.S. Appl. No. 12/749,109 dated Apr. 15, 2013.
Office Action issuedin U.S. Appl. No. 12/749,109 dated Aug. 4, 2011.

(56) References Cited

OTHER PUBLICATIONS

Office Action issued in U.S. Appl. No. 12/749,109 dated Dec. 28, 2012.
Office Action issued in U.S. Appl. No. 12/749,109 dated Feb. 18, 2011.
Office Action issued in U.S. Appl. No. 12/749,109 dated Jan. 17, 2012.
Office Action issued in U.S. Appl. No. 13/423,696 dated Apr. 16, 2013.
Office Action issued in U.S. Appl. No. 13/423,696 dated Sep. 25, 2012.
Office Action, dated Nov. 16, 2015, U.S. Appl. No. 14/198,127.
Office Action dated Jun. 28, 2016 in U.S. Appl. No. 14/996,548 (14 pages).
Office Action, dated Apr. 2, 2015, U.S. Appl. No. 14/198,127.
Office Action, dated Apr. 28, 2016, U.S. Appl. No. 14/198,127.
Office Action, dated Apr. 8, 2015, U.S. Appl. No. 13/423,696.
Office Action, dated Dec. 26, 2014, U.S. Appl. No. 13/423,696.
Office Action, dated Mar. 3, 2014, U.S. Appl. No. 13/423,696.

\* cited by examiner

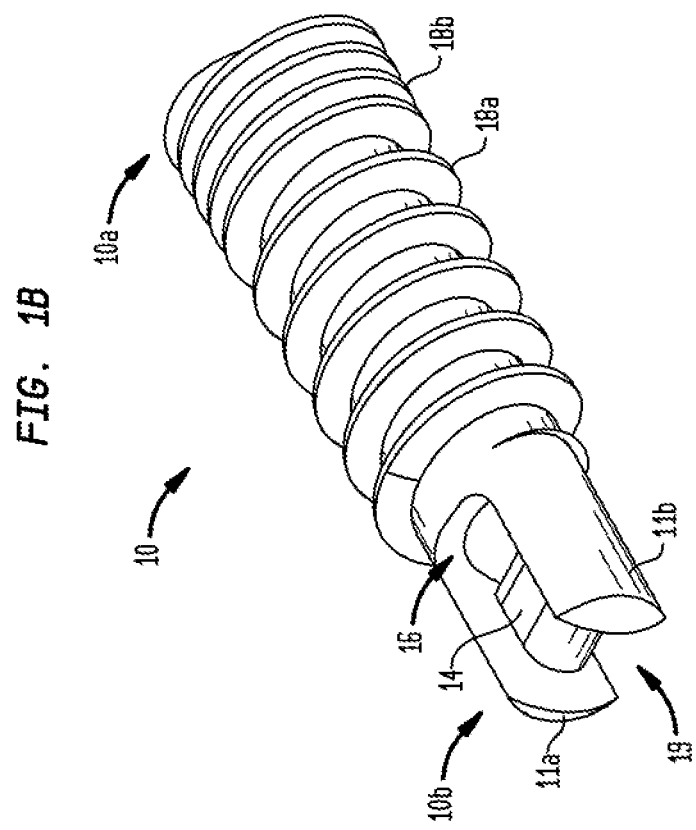
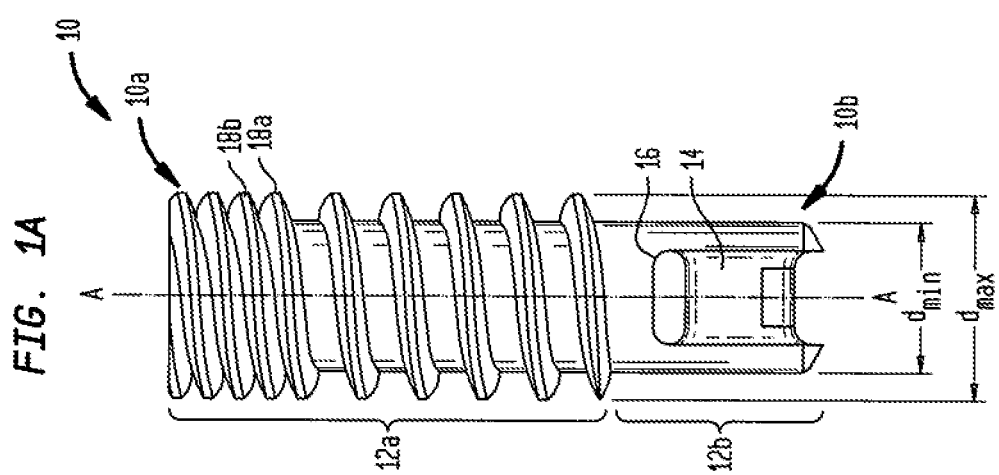

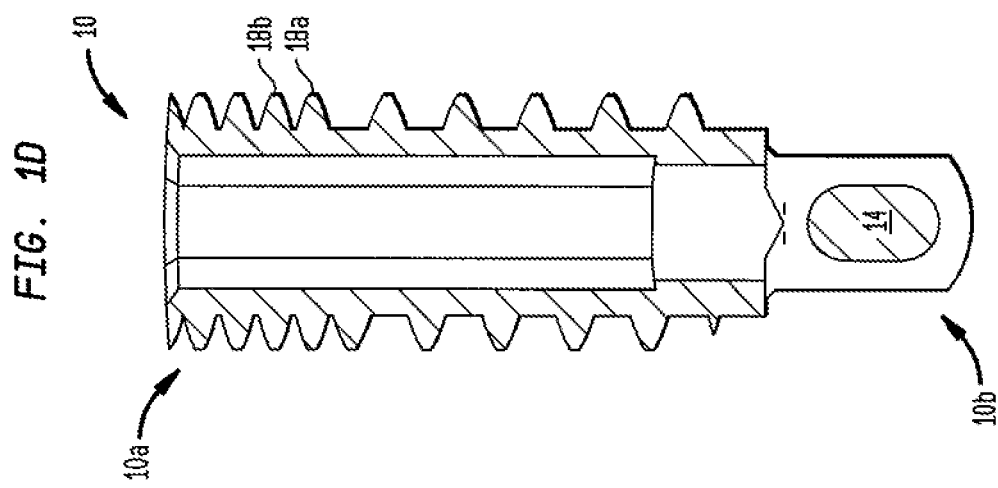
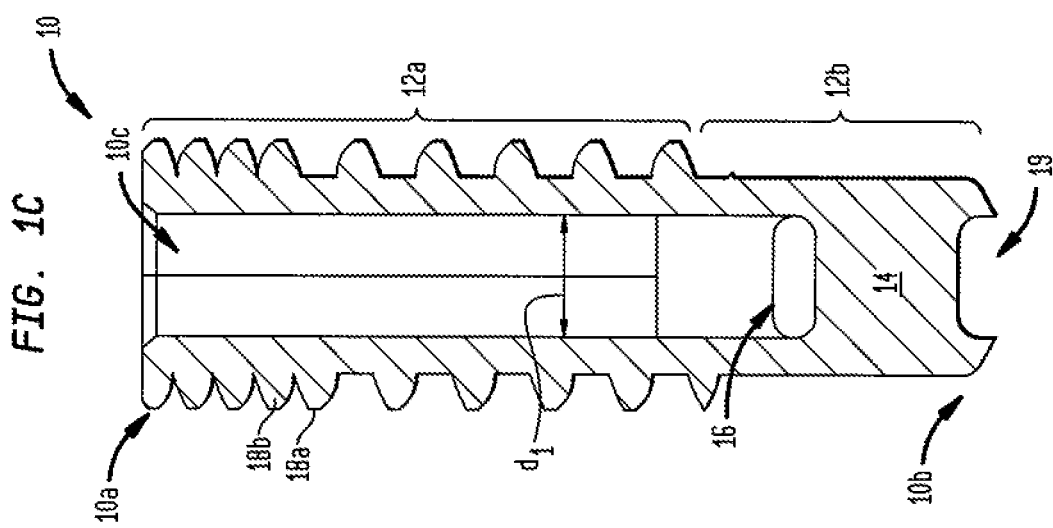

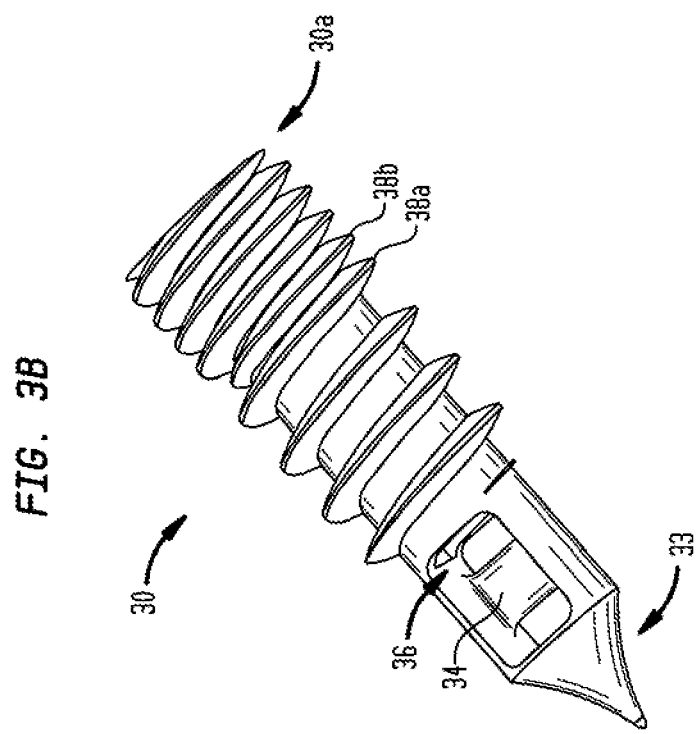
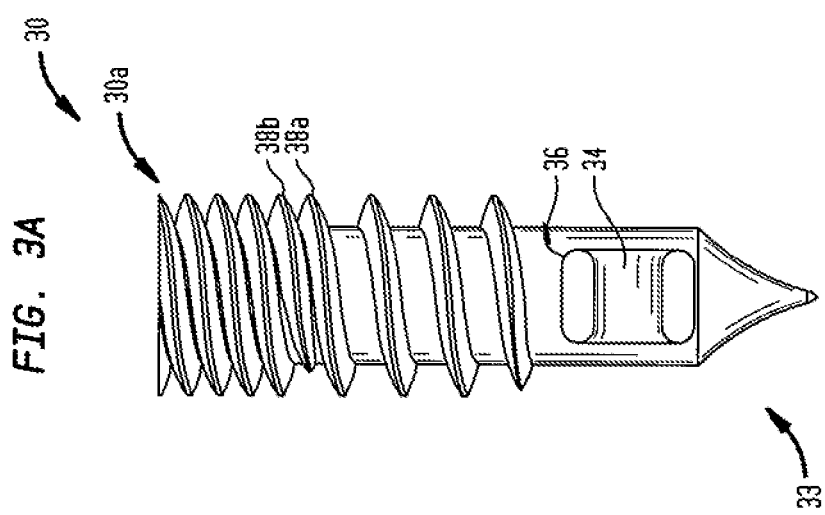

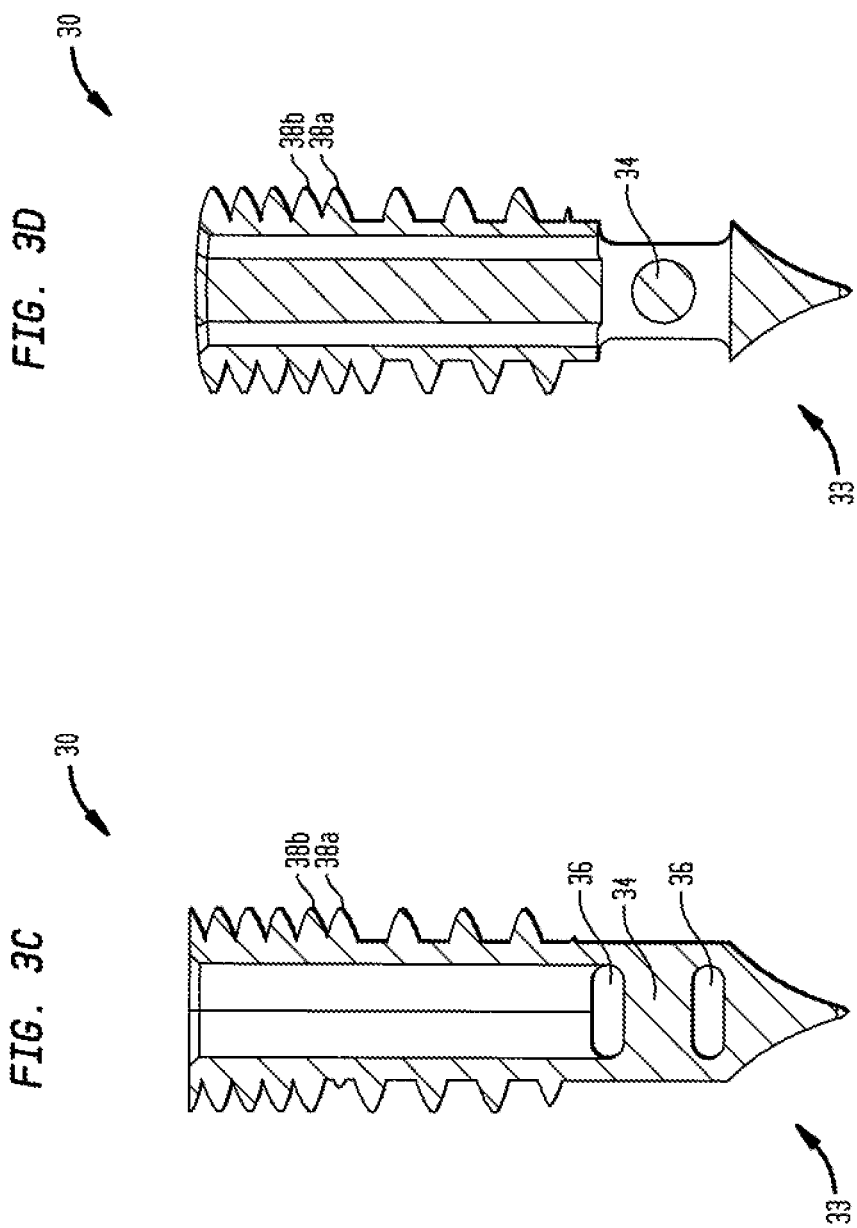

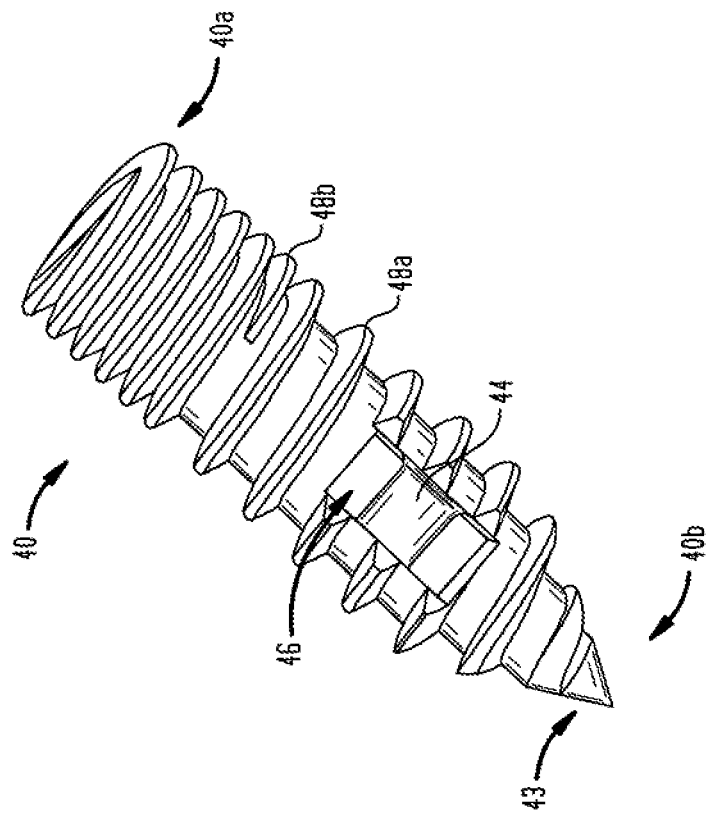
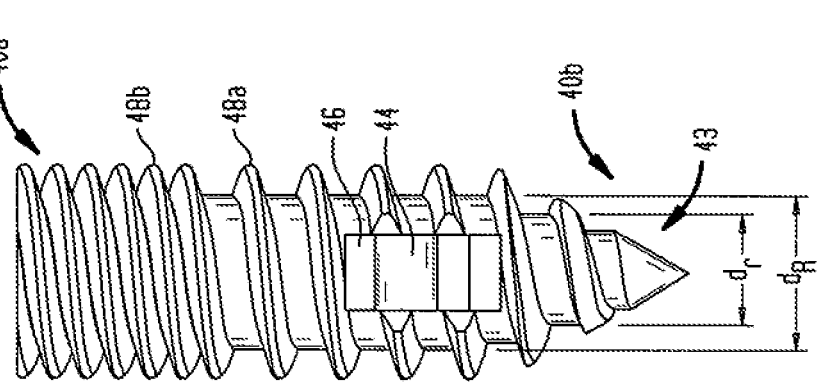

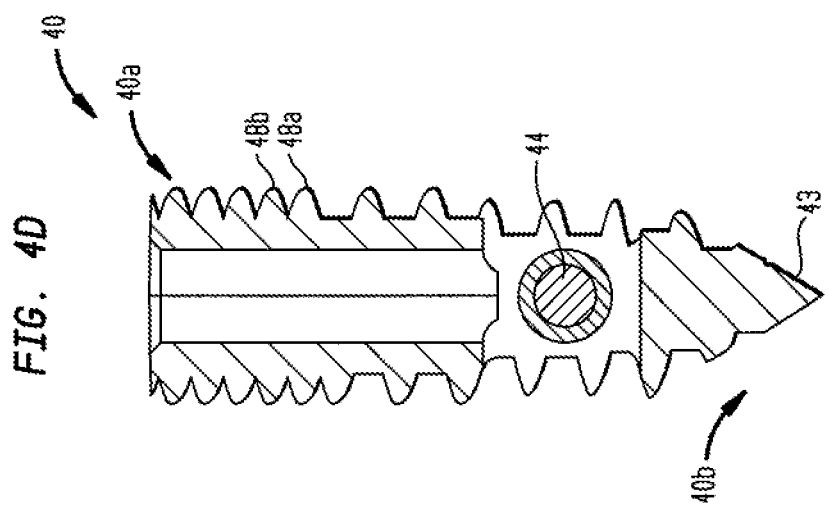
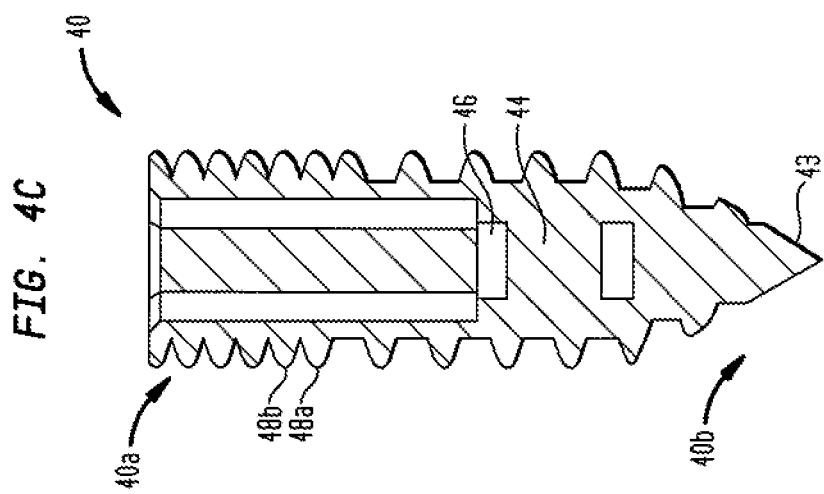

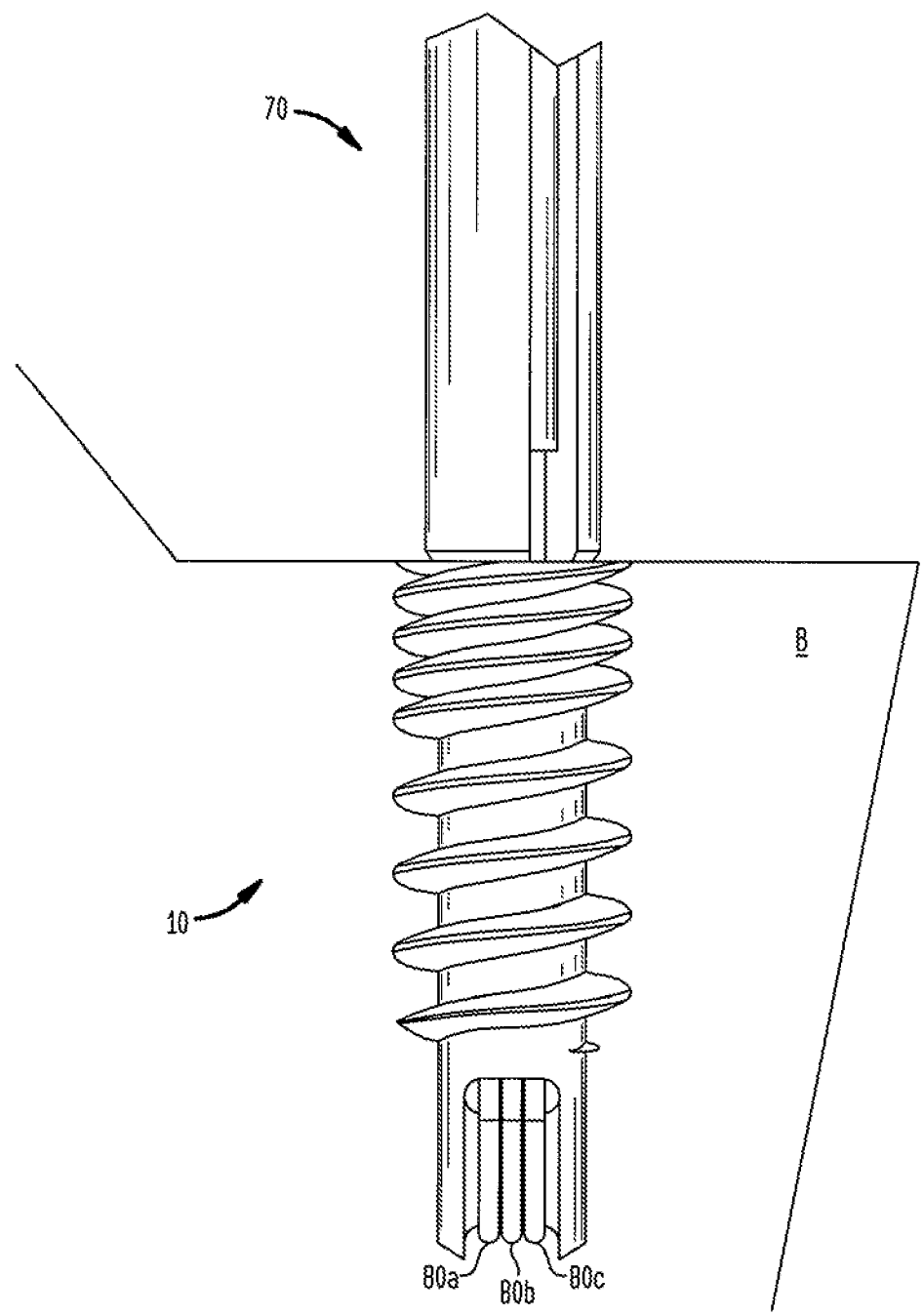

METHODS FOR ANCHORING SUTURE TO BONE

CROSS-REFERENCE TO RELATED APPLICATIONS

The present application is a continuation of U.S. patent application Ser. No. 14/198,127, now U.S. Pat. No. 10,327, 752, filed Mar. 5, 2014 and entitled "METHODS FOR ANCHORING SUTURE TO BONE," which is a continuation of U.S. patent application Ser. No. 11/855,728, now U.S. Pat. No. 8,702,754, filed Sep. 14, 2007 and entitled "METHODS FOR ANCHORING SUTURE TO BONE" and U.S. patent application Ser. No. 11/855,670, now U.S. Pat. No. 8,882,801, filed Sep. 14, 2007 and entitled "DUAL THREAD CANNULATED SUTURE ANCHOR", which are hereby incorporated by reference in their entirety.

FIELD OF THE INVENTION

The present invention generally relates to medical devices and procedures, and more particularly to systems and methods for attaching soft tissue to bone.

BACKGROUND OF THE INVENTION

The complete or partial detachment of ligaments, tendons and/or other soft tissues from their associated bones within the body are relatively commonplace injuries, particularly among athletes. Such injuries are generally the result of excessive stresses being placed on these tissues. By way of example, tissue detachment may occur as the result of an accident such as a fall, over-exertion during a work-related activity, during the course of an athletic event, or in any one of many other situations and/or activities.

In the case of a partial detachment, the injury will frequently heal itself, if given sufficient time and if care is taken not to expose the injury to further undue stress. In the case of complete detachment, however, surgery may be needed to re-attach the soft tissue to its associated bone or bones. Numerous devices are currently available to re-attach soft tissue to bone. Examples of such currently-available devices include screws, staples, suture anchors, and tacks. In soft tissue re-attachment procedures utilizing screws, the detached soft tissue is typically moved back into its original position over the bone. Then the screw is screwed through the soft tissue and into the bone, with the shank and head of the screw holding the soft tissue to the bone. Similarly, in soft tissue re-attachment procedures utilizing staples, the detached soft tissue is typically moved back into its original position over the bone. Then the staple is driven through the soft tissue and into the bone, with the legs and bridge of the staple holding the soft tissue to the bone.

In soft tissue re-attachment procedures utilizing suture anchors, an anchor-receiving hole is generally first drilled in the bone at the desired point of tissue re-attachment. Then a suture anchor is deployed in the hole using an appropriate installation tool. This effectively locks the suture to the bone, with the free end(s) of the suture extending out of the bone. The free ends of the suture are passed through or around the soft tissue and are used to tie the soft tissue securely to the bone.

While current suture anchors are effective in anchoring soft tissue to bone, one drawback with current devices is that the suture anchor must have a head with a length that is sufficient to withstand a torque applied thereto by a driver. As a result of the increased length, the suture anchor will typically extend at least partially into underlying soft cancellous bone in order to position the head beneath the outer surface of the bone. The bone-engaging portion of the suture anchor will thus be mostly disposed within and engaged with cancellous bone, rather than cortical bone. This is due to the fact that the cortical bone is only about 1 mm to 3 mm in length, and the driver head is often longer than 3 mm. Once implanted, tension applied to the anchor via the sutures can cause the anchor to migrate into the cortical bone and thus the head of the suture anchor can become proud, resulting in a weak fixation among other problems.

Accordingly, there remains a need for improved methods and devices for attaching soft tissue to bone.

SUMMARY OF THE INVENTION

Methods and devices are provided for anchoring sutures to bone. In one embodiment, a suture anchor is provided having an elongate body with proximal and distal ends and an inner lumen extending therethrough. A first thread extends around the elongate body from the proximal end toward the distal end of the elongate body, and a second thread extends around the elongate body between at least a portion of the first thread such that the first and second threads are spaced a distance apart from one another. In an exemplary embodiment, the elongate body has a constant root diameter. The suture anchor can also include a suture-engaging member located adjacent to the distal end of the elongate body and positioned such that a suture can be disposed therearound and trailing ends of the suture can extend through the inner lumen and out of the proximal end of the elongated body.

The first and second threads can have various configurations. In one embodiment, the first thread can extend from the proximal end to a position just proximal to the suture-engaging member, and the second thread can extend from the proximal end and terminate proximal to the first thread. In another embodiment, the first and second threads can extend from the proximal end to a position just proximal to the suture-engaging member such that the first and second threads have a length that is substantially the same. Alternatively, the first thread can extend from the proximal end to the distal end, and the second thread can extend from the proximal end and terminate proximal to the first thread. In another embodiment, the first and second threads can extend from the proximal end to the distal end such that the first and second threads have a length that is substantially the same and that extends along an entire length of the elongate body.

The suture anchor can also include various other features. For example, the suture anchor can include a distal tip formed on the distal end of the suture anchor. The threads can be formed on the distal tip, or the distal tip can be non-threaded. The tip can also be blunt or it can be pointed to facilitate insertion into a bone hole, and the tip can be hollow or solid. In other embodiments, the suture anchor can include a proximal end that is configured to receive a driver. For example, a proximal portion of the inner lumen can have an asymmetrical or non-circular cross-sectional shape for receiving a driver tool therein.

The suture-engaging member can also have a variety of configurations. In an exemplary embodiment, the suture-engaging member extends between opposed walls of the inner lumen, preferably substantially perpendicular to a longitudinal axis of the lumen. The suture-engaging member can have various shapes and sizes. For example, in one embodiment the suture-engaging member include features, such as scallops, to facilitate positioning of multiple sutures.

In yet another embodiment, a suture anchor is provided having an elongate body with first and second threads extending from a proximal end toward a distal end of the elongate body, an inner lumen extending into a proximal end of the elongate body, and a cut-out formed in a sidewall of the elongate body. The cut-out is in communication with the inner lumen and it defines a suture-engaging member extending across the inner lumen and configured such that a suture can extend around the suture-engaging member and trailing ends of the suture can extend through the cannulated body.

In other aspects, a suture anchor is provided having a cannulated body with first and second threads extending from a proximal end toward a distal end of the cannulated body, an opening formed in a sidewall of the cannulated body and in fluid communication with an inner lumen extending through the elongate body, and a suture-engaging member extending across the inner lumen and configured such that a suture can extend around the suture-engaging member and trailing ends of the suture can extend through the cannulated body.

Exemplary suture anchor systems are also provided, and in one embodiment the system can include a suture anchor having a cannulated body with first and second threads extending from a proximal end toward a distal end of the cannulated body, and a suture-engaging member located adjacent to the distal end and configured such that a suture can extend around the suture-engaging member and trailing ends of the suture can extend through the cannulated body. The system can also include a driver tool having a distal end adapted to be inserted into and to engage the proximal end of the suture anchor for driving the suture anchor into bone.

The threads can have various configurations. In one embodiment, the second thread can have a distal end that terminates at a location proximal to a distal end of the first thread. Alternatively, the first and second threads can have a length that is substantially the same. The suture anchor can also include various other features, including those previously discussed above.

Exemplary methods for anchoring suture to bone are also provided. In one embodiment, a method for anchoring suture to bone includes coupling a suture to a suture anchor such that the suture extends around a suture-engaging member formed in a distal portion of the suture anchor and trailing ends of the suture extend through an inner lumen extending through the suture anchor and out of a proximal end of the suture anchor. A driver is inserted into the proximal end of the suture anchor, and the driver is rotated to thread the suture anchor into a bone hole to anchor the suture to the bone. In an exemplary embodiment, the suture anchor includes an opening formed in a sidewall thereof that allows fluid to flow into the inner lumen of the suture anchor. The suture anchor can include first and second threads that are spaced axially apart from one another and that have the same pitch such that the first and second threads are driven into bone at the same rate. In one embodiment, the first and second threads can be formed on at least the proximal portion of the suture anchor such that the first and second threads engage cancellous bone. In another embodiment, the first thread can extend along a distal portion of the suture anchor such that the first thread engages cortical and cancellous bone. In yet another embodiment, the first and second threads can extend from the proximal end to the distal end of the suture anchor such that the first and second threads engage cortical and cancellous bone.

BRIEF DESCRIPTION OF THE DRAWINGS

The invention will be more fully understood from the following detailed description taken in conjunction with the accompanying drawings, in which:

FIG. 1A is a side view of one embodiment of a cannulated suture anchor having a proximal portion with a dual threaded region and a single threaded region, and a non-threaded distal portion with a suture-engaging member;

FIG. 1B is a perspective view of the cannulated suture anchor of FIG. 1A;

FIG. 1C is a cross-sectional view of the cannulated suture anchor of FIG. 1A;

FIG. 1D is another cross-sectional view of the cannulated suture anchor of FIG. 1A;

FIG. 3A is a side view of yet another embodiment of a cannulated suture anchor having a proximal portion with a dual threaded region and a single threaded region, and a non-threaded distal portion with a suture-engaging member and a bone-penetrating tip;

FIG. 3B is a perspective view of the cannulated suture anchor of FIG. 3A;

FIG. 3C is a cross-sectional view of the cannulated suture anchor of FIG. 3A;

FIG. 3D is another cross-sectional view of the cannulated suture anchor of FIG. 3A;

FIG. 4A is a side view of a cannulated suture anchor having a dual threaded proximal portion and a single threaded distal portion with a suture-engaging member and a bone-penetrating tip according to another embodiment;

FIG. 4B is a perspective view of the cannulated suture anchor of FIG. 4A;

FIG. 4C is a cross-sectional view of the cannulated suture anchor of FIG. 4A;

FIG. 4D is another cross-sectional view of the cannulated suture anchor of FIG. 4A;

FIG. 8 is a partially cross-sectional view of the suture anchor of FIG. 1A implanted in bone and having three sutures coupled thereto.

DETAILED DESCRIPTION OF THE INVENTION

Figure 2B:
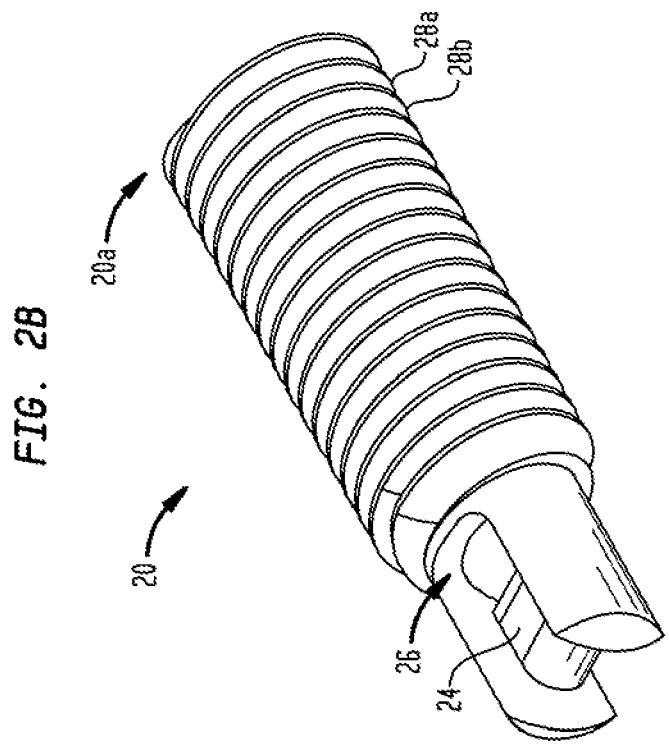
FIG. 2B is a perspective view of the cannulated suture anchor of FIG. 2A.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides methods and devices for anchoring suture to bone. In an exemplary embodiment, a cannulated suture anchor is provided and includes a suture-engaging member formed therein or thereon and configured to receive a suture therearound such that trailing ends of the suture can extend through the suture anchor. The use of a cannulated suture anchor allows a driver to be inserted into the inner lumen of the suture anchor for driving the suture anchor into bone. Such a configuration will allow the torque strength of the suture anchor to be maximized due to the increased engagement between the suture anchor and the driver. This in turn will allow the suture anchor to be formed from a broad range of materials, including nonabsorbable materials, such as metal or plastic, bioabsorbable materials, and/or osteoconductive materials. The cannulated suture anchor is also particularly advantageous as the inner lumen can allow materials, such as bone-growth promoting materials, sealants, adhesives, etc., to be introduced therein to facilitate fixation. The suture anchor can also include at least a proximal portion with dual threads configured to optimize fixation within hard cortical bone, thereby decreasing the risk for migration of the suture anchor. A person skilled in the art will appreciate that, while methods and devices are disclosed herein for anchoring soft tissue to bone, the methods and devices can be used in a variety of other medical procedures for anchoring various objects to one another.

FIGS. 1A-1D illustrate one exemplary embodiment of a cannulated suture anchor 10 for anchoring soft tissue to bone. As shown, the suture anchor 10 is in the form of a generally elongate body having proximal and distal ends 10a, 10b with an inner lumen 10c extending therethrough. At least one bone-engaging surface feature can be formed on at least a portion of an external surface thereof for engaging bone. In the illustrated embodiment, the suture anchor 10 includes a threaded proximal portion 12a and a non-threaded distal portion 12b. The suture anchor 10 also includes a suture-engaging member 14 disposed within the inner lumen 10c adjacent to the distal end 10b of the suture anchor 10. The suture-engaging member 14 can be adapted to receive one or more sutures therearound such that the suture(s) can extend around the suture-engaging member 14 and trailing ends of the suture(s) can extend through the inner lumen 10c and out of the proximal end 10a of the suture anchor 10.

The suture anchor 10 can be formed from a variety of materials. In an exemplary embodiment, the material has physical properties that are sufficient to allow a driver to be inserted into the inner lumen 10c of the suture anchor 10 and to be used to drive the suture anchor 10 into bone without damaging the suture anchor 10. The properties of the material will of course depend on the particular configuration of the suture anchor 10. For example, the inner lumen 10c of the suture anchor 10 can have a length that maximizes the torque strength of the suture anchor 10 as well as the amount of surface contact between a driver and the suture anchor 10, thus allowing weaker materials, such as bioabsorbable and/or osteoconductive materials to be used. A person skilled in the art will appreciate that a variety of other materials, including plastics and metals, can be used to form the suture anchor 10.

The body of the suture anchor 10 can have a variety of configurations, shapes, and sizes. In an exemplary embodiment, the body is configured to be implanted within a bone tunnel formed in bone, and more preferably it has a size and shape that allows it to be fully engaged through the thickness of the cortical bone. As indicated above, in the illustrated embodiment the body has a generally elongate cylindrical shape with an inner lumen 10c extending therethrough. The diameter di of the inner lumen 10c can vary, but in an exemplary embodiment the diameter di is sufficient to receive one or more, and preferably three, pairs of sutures therethrough. In an exemplary embodiment, the inner lumen 10c has a diameter di that is in the range of about 1.5 mm to 3.0 mm. This will allow six trailing ends of three sutures having a maximum outer diameter of about 0.028 inches each to be disposed through the inner lumen 10c. As further shown in FIGS. 1A-1D, the inner 10c lumen can extend through the entire length of the suture anchor 10, including through the distal tip as will be discussed in more detail below. The suture-engaging member 14 can, however, extend across a portion of the lumen 10c, as will be discussed in more detail below. In other embodiments, the lumen 10c can terminate prior to a substantially solid tip. The tip can be blunt or rounded, as shown, or it can be pointed to facilitate insertion into a bone tunnel. Other tip configurations can be utilized, as later disclosed herein or as known in the art.

The proximal end 10a of the body can be head-free, as the cannulated configuration of the body allows a driver to be inserted into the inner lumen 10c to drive the suture anchor 10 into bone. While various techniques can be used to facilitate engagement between the inner lumen 10c and a driver mechanism, in an exemplary embodiment the inner lumen 10c, or at least a portion thereof, has an asymmetrical or non-circular shape that complements a corresponding asymmetrical or non-circular shape of a driver. The asymmetrical portion preferably extends along a substantial length of the inner lumen 10c so as to maximum surface contact between a driver and the suture anchor 10. By way of non-limiting example, FIGS. 1C and 1D illustrate a hexagonal cross-sectional shape formed in the inner lumen 10c for receiving a driver having a corresponding hexagonal drive tip. The hexagonal cross-section extends from the proximal-most end 10a of the suture anchor 10 and terminates just proximal to the proximal end of a cut-out 16, as will be discussed in more detail below. Exemplary drivers are discussed in more detail below, and are also disclosed in commonly-owned U.S. application Ser. No. 11/555,545 filed on Nov. 1, 2006 and entitled "Cannulated Suture Anchor," U.S. application Ser. No. 11/555,557 filed on Nov. 1, 2006 and entitled "Suture Anchor With Pulley," and U.S. application Ser. No. 11/555,568 filed on Nov. 1, 2006 and entitled "Wired Sutures," all of which are hereby incorporated by reference in their entireties.

As further shown in FIGS. 1A-1D, the body can also include one or more bone-engaging surface features formed thereon and adapted to engage bone. While various surface features can be used, such as teeth, ridges, protrusions, etc., in an exemplary embodiment the body can include one or more threads extending therearound, and more preferably the threads are formed on at least a proximal portion of the body to provide enhanced fixation with hard cortical bone to prevent migration of the suture anchor when implanted. As shown in FIGS. 1A-1D, the body includes a threaded proximal portion 12a having a first and second threads 18a, 18b extending therearound and a non-threaded distal portion 12b. The first thread 18a originates at the proximal end 10a of the body and it terminates just proximal to the suture-engaging member 14. The particular location at which the first thread 18*a* terminates can vary depending on the particular configuration of the suture anchor 10, as well as the configuration of the tip. As will be discussed in more detail below, the illustrated suture anchor 10 can include a cut-out 22 formed in the distal end 10*b* thereof and the first thread 18*a* can terminate just proximal to the proximal end of the cut-out 22. As a result, the first thread 18*a* extends along about 75% of the length of the suture anchor 10. A person skilled in the art will appreciate, however, that the length of the first thread 18*a* can vary. As further shown in FIGS. 1A-1D, the body can also include a second thread 18*b* extending between the first thread 18*a*. The second thread 18*b* can extend over only a portion of the body, or over the entire length of the body, including or excluding the distal tip, as will be discussed in more detail below. As shown in FIGS. 1A-1D, the second thread 18*b* extends along only a proximal-most portion of the body, and it terminates proximal to the first thread 18*a*. The illustrated second thread 18*b* thus extends over about 25% of the length of the suture anchor 10. As a result, the illustrated suture anchor 10 includes a threaded proximal portion 12*a* with a dual threaded proximal region and a single threaded distal region.

While the position of the second thread 18*b* relative to the first thread 18*a* can vary, in an exemplary embodiment, as shown, the second thread 18*b* extends between the first thread 18*a* and the threads 18*a*, 18*b* are spaced equidistant apart from one another along the axis A of the suture anchor 10, i.e., the threads 18*a*, 18*b* are axially aligned. The first and second threads 18*a*, 18*b* can also have the same or different configurations, but in an exemplary embodiment the first and second threads 18*a*, 18*b* are identical and have the same shape and size, including the same pitch. This will allow the first and second threads 18*a*, 18*b* to simultaneously cut independent courses (paths) through bone. While the pitch can vary depending on the particular configuration of the suture anchor as well as the intended use, in an exemplary embodiment the pitch is in the range of about 8 TPI to 20 TPI, and more preferably the pitch is about 15 TPI. The first and second threads 18*a*, 18*b* can also be aligned radially with one another, or alternatively the second thread 18*b* can be radially offset from the first thread 18*a* such that one of the threads, e.g., the first thread 18*a*, engages bone prior to the other thread, e.g., the second thread 18*b*, to facilitate insertion.

The geometry of each thread 18*a*, 18*b* can also vary, and the threads 18*a*, 18*b* can have a constant thickness between the root and crest, or the thickness can decrease from the root to the crest as shown. The shape of the crest can also vary. As shown in FIGS. 1A-1D, the threads 18*a*, 18*b* each have a v-shaped configuration with opposed surfaces that extend at about 40° and with a flat crest. Such a configuration facilitates engagement with bone, thereby preventing suture migration when the anchor 10 is implanted.

As further shown in FIGS. 1A-1D, the suture anchor 10 can also have a minor or root diameter dmin that remains constant along the entire length thereof, or at least along the threaded portion. The major diameter dmax can also remain constant along the entire length of the suture anchor 10. While the particular dimensions will vary depending on the size of the suture anchor and the intended application, in an exemplary embodiment the suture anchor 10 has major and minor diameters dmax, dmin that differ by about 1-2 mm, and more preferably about 1.5 mm. For example, the major diameter can be about 5.5 mm, and the minor diameter can be about 4 mm. A person skilled in the art will appreciate that the major and/or minor diameters can also vary, and they can taper along a portion or along the entire length of the suture anchor 10.

As previously indicated above, the suture anchor 10 can also include a suture-engaging member 14. The suture-engaging member 14 can have a variety of configurations, but in an exemplary embodiment it is adapted to engage one or more sutures that extend through the inner lumen 10*c* of the suture anchor 10. As shown in FIGS. 1A-1D, the suture-engaging member 14 is in the form of a post or elongate member that extends transversely across the inner lumen 10*c* between opposed inner sidewalls of the suture anchor 10. The angular orientation of the suture-engaging member 14 relative to the longitudinal axis A of the suture anchor 10 can vary, but in an exemplary embodiment the suture-engaging member 14 extends substantially perpendicular to the longitudinal axis A of the anchor 10. The location of the suture-engaging member 14 can also vary, but in an exemplary embodiment the suture-engaging member 14 is positioned at or adjacent to the distal end 10*b* of the suture anchor 10. In the embodiment shown in FIGS. 1A-1D, the suture-engaging member 14 is located just proximal to the distal-most end 10*b* of the suture anchor 10 so as to form a suture-seating groove 19 in the distal-most end of the suture anchor 10. This recessed configuration of the suture-engaging member 14 can allow a suture(s) disposed around the suture-engaging member 14 to sit flush or sub-flush with the distal end 10*b* of the suture anchor 10 such that the suture(s) will not interfere with insertion of the suture anchor 10 into bone. The location of the suture-engaging member 14 near the distal end 10*b* is also advantageous as it allows the remainder of the lumen extending proximally from the suture-engaging member 14 to receive the driver. A person skilled in the art will appreciate that the suture-engaging member 14 can be integrally formed with the suture anchor 10, i.e., the suture anchor 10 and suture-engaging member 14 can be molded as a single unit or formed from a single piece of material, or the suture-engaging member 14 can be fixedly or removably mated to the suture anchor 10.

As further shown in FIGS. 1A-1D, in order to facilitate positioning of a suture(s) around the suture-engaging member 14, the suture anchor 10 can include one or more cut-outs formed in a sidewall thereof adjacent to the suture-engaging member 14. As best shown in FIGS. 1A and 1B, in an exemplary embodiment the suture anchor 10 includes a cut-out 16 that begins just proximal to the location of the suture-engaging member 14, and that extends around the distal end 10*b* of the suture anchor 10 such that the suture anchor 10 includes opposed cut-outs or openings formed on opposed sides of the suture-engaging member 14 and a distal cut-out that defines the suture-seating groove 19 for seating a suture(s). The cut-out 16 can also define opposed distal arms 11*a*, 11*b* on the suture anchor 10 that are spaced a distance apart from one another and that have the suture-engaging member 14 extending therebetween.

A person skilled in the art will appreciate that the particular location and configuration of the cut-out 16 can define the particular location and configuration of the suture-engaging member 14, as the cut-out 16 can be formed during manufacturing to create the suture-engaging member 14. Alternatively, the particular location and configuration of the opposed arms 11*a*, 11*b* can define the particular location and configuration of the cut-out 16, as the shape and size of the arms 11*a*, 11*b* defines the shape and size of the cut-out 16. The location of the suture-engaging member 14 relative to the cut-out 16 and/or arms 11*a*, 11*b* will also define the configuration of the distal end of the suture anchor 10, and whether the suture anchor 10 includes a distal groove 19 for seating a suture(s).

A person skilled in the art will also appreciate that the suture-engaging member 14 can have a variety of other configurations, and that it can be fixed or movable, e.g., rotatable and/or slidable. Various exemplary configurations are disclosed herein, and in more detail in the commonly-owned U.S. applications previously referenced herein.

Figure 2A:
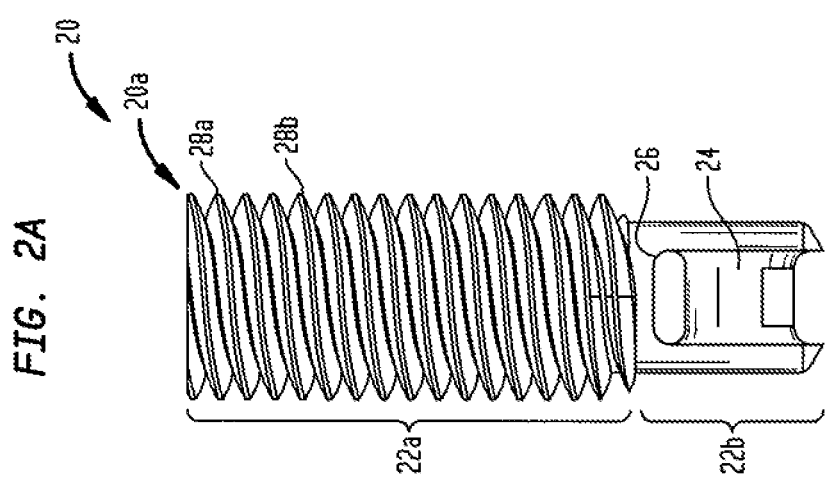
FIG. 2A is a side view of another embodiment of a cannulated suture anchor having a dual threaded proximal portion and a non-threaded distal portion with a suture-engaging member.

As indicated above, while FIGS. 1A-1D illustrate a second thread 18b having a length that is less than a length of the first thread 18a, in other embodiments the first and second threads can have the same length. FIGS. 2A-2B illustrate another embodiment of a suture anchor 30 having first and second threads 28a, 28b that have the same length. In particular, the first and second threads 28a, 28b originate at the proximal end 20a and they both terminate at a location just proximal to the suture-engaging member 24, or to the cut-out 26 formed in the body. The first and second threads 28a, 28b thus extend along about 75% of the length of the suture anchor 20. Such a configuration is particularly advantageous as the dual threads will improve fixation, especially within the cancellous bone which is engaged by the proximal portion 22a of the anchor. The distal portion 22b of the anchor 20 can be non-threaded, and can have the same configuration as previously discussed with respect to FIGS. 1A-1D, or it can have a variety of other configurations as discussed herein or known in the art.

In yet another embodiment, shown in FIGS. 3A-3D, the suture anchor 30 can include a pointed tip 33 to facilitate penetration into bone. As shown, the distal tip 33 can have a solid, pointed configuration, and it can form the distal-most end of the suture anchor 30. The suture-engaging member 34 can thus be positioned proximal to the distal tip 33, and the cut-out 36 can be in the form of a cavity extending through opposed walls of the suture anchor 30, as best shown in FIGS. 3C and 3D. The remainder of the suture anchor 30 can be similar to the anchor previously discussed with respect to FIGS. 1A-1D. In general, the suture anchor 30 can include a first thread 38a that extends from the proximal end 30a to a position just proximal to the cut-out 36, and a second thread 38b that is disposed between the first thread 38a and that extends from the proximal end 30a and terminates proximal to the first thread 38a.

Alternatively, the threads can extend along the entire length of the suture anchor. FIGS. 4A-4D illustrate another embodiment of a suture anchor 40 having a first thread 48a that extends along the entire length from the proximal end 40a to the distal end 40b. The first thread 48a thus extends toward and can run-out at the pointed tip 43. The second thread 48b can extend along only a proximal portion of the anchor 40, as shown in FIGS. 4A-4D, or it can alternatively likewise extend along the entire length. A person skilled in the art will appreciate that the particular configurations of the threads, as well as the configuration of the distal tip, can vary and virtually and combination of features can be combined to form an anchor as may be desired. As further shown in FIGS. 4A-4D, in order to allow the thread 48a to extend along the distal-most portion, i.e., to extend distally beyond the cut-out 46 and suture engaging member 44, the cut-out 46 and suture-engaging member 44 can be located more toward the mid-portion of the anchor. As a result, the cut-out 46 extends through the threads. As is also shown in FIGS. 4A-4D, the portion of the body located distal to the cut-out 46 can have a root or minor diameter $d_r$ that is less than the root or minor diameter $d_R$ of the remaining proximal portion of the anchor. This will form a smaller tip to facilitate impaction into bone.

Figure 5B:
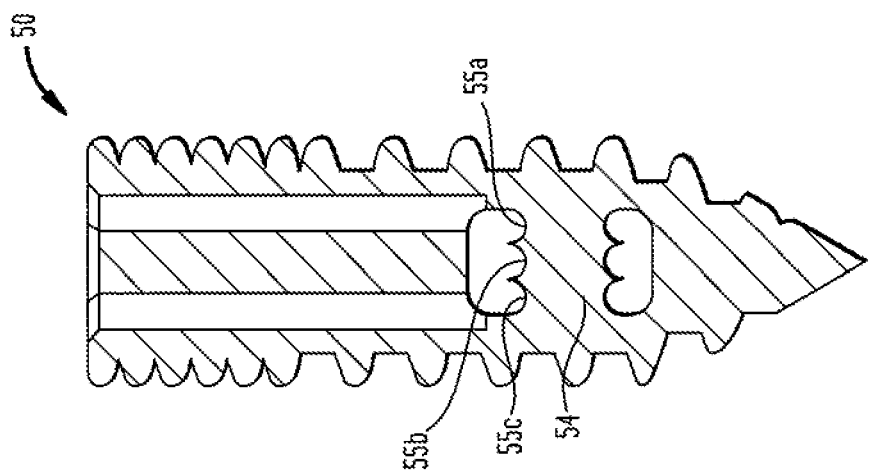
FIG. 5B is a cross-sectional view of the cannulated suture anchor of FIG. 5A.
Figure 5A:
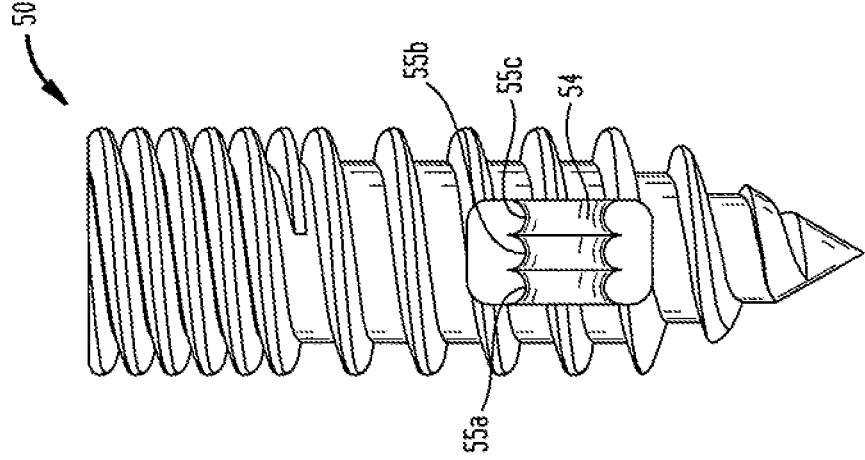
FIG. 5A is a side view of yet another embodiment of a cannulated suture anchor having a proximal portion with a dual threaded region and a single threaded region, a threaded distal portion having a pointed tip, and a scalloped suture-engaging member.

FIGS. 5A and 5B illustrate another embodiment of a suture anchor 50. In this embodiment, the suture anchor 50 is similar to anchor 40, except that the suture-engaging member 54 is scalloped to facilitate sliding movement of the sutures while preventing entanglement. While the number of scallops can vary depending on the number of sutures used with the anchor, in the illustrated embodiment the suture-engaging member 54 includes two scallops that defines three suture-seating grooves 55a, 55b, 55c. Thus, three sutures can be positioned around the suture-engaging member 54, with each suture resting in a groove 55a, 55b, 55c. Each suture can thus be individually slid relative to the suture-engaging member 54 without causing movement of an adjacent suture. The scallops can also help maintain alignment of the sutures as they extend through the anchor 50, thereby preventing entanglement. A person skilled in the art will appreciate that a variety of other techniques can be used to help maintain alignment of the sutures, prevent entanglement, and/or facilitate sliding movement. For example, the suture-engaging member can include one or more pathways formed therethrough, with each pathway being configured to receive a suture.

Figure 6:
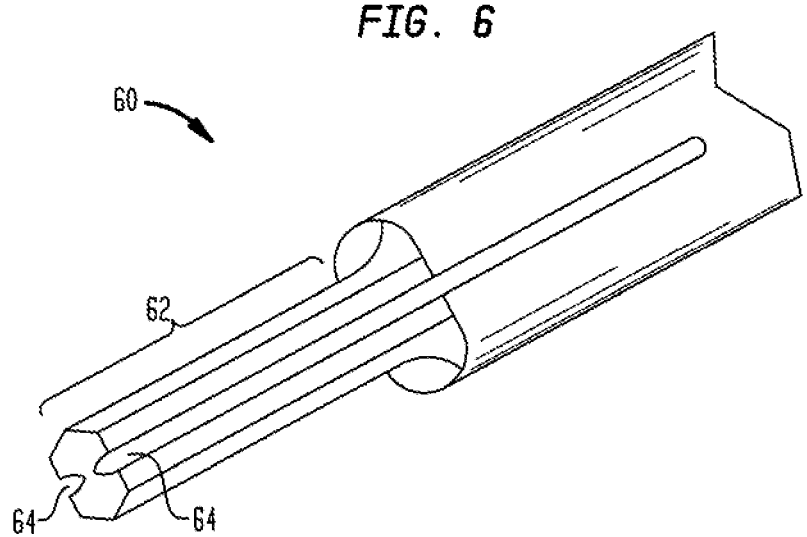
FIG. 6 is a perspective view of one embodiment of a driver tool for inserting a suture anchor into bone.
Figure 7:
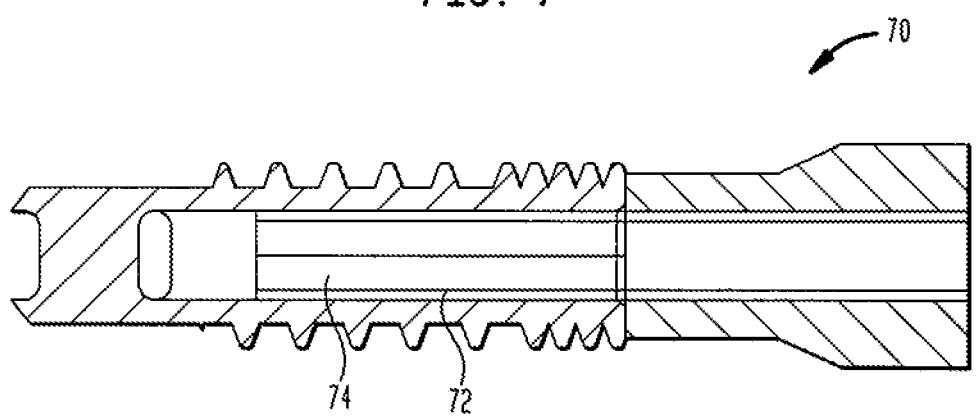
FIG. 7 is a cross-sectional view of another embodiment of a driver tool shown engaged with a suture anchor.

As previously indicated, in use the various suture anchors disclosed herein can be configured to receive one or more sutures, and to receive a driver for driving the anchor into bone to thereby anchor the suture to bone. While various drivers can be used, FIGS. 6 and 7 illustrate two exemplary embodiments of drivers that are particularly configured for use with the suture anchors disclosed herein. Referring first to FIG. 6, as shown the driver 60 has a generally elongate shaft with a drive tip 62 formed on a distal end thereof. The drive tip 62 has a shape and size that corresponds to the shape and size of the suture anchor. In particular, in the illustrated embodiment the drive tip 62 has a hexagonal cross-sectional shape that allows the tip 62 to be disposed within and to engage a hexagonal lumen formed in a suture anchor, such as anchor 10 of FIGS. 1A-1D. The length of the drive tip 62 can vary, but preferably the length is maximized to provide enhanced surface contact between the drive tip 62 and the suture anchor. In an exemplary embodiment, the drive tip 62 has a length that is configured such that the drive tip 62 can extend from the proximal end of the suture anchor and can terminate just proximal to the suture-engaging member. As further shown in FIG. 6, the drive tip 62 can also include one or more suture-seating grooves 64 formed therein and configured to seat the terminal ends of the suture so as to prevent engagement of the suture between the drive tip 62 and the suture anchor. While FIG. 6 illustrates two opposing suture-seating grooves 64, the drive tip 62 can include any number of grooves, and the shape and size of each groove can vary depending on the quantity of sutures used with the suture anchor. In another embodiment, shown in FIG. 7, the driver 70 can be cannulated to allow the sutures to extend through the inner lumen 74 of the drive tip 72 and through the elongate shaft of the driver, rather than along an external surface of the drive tip 72. A person skilled in the art will appreciate that a variety of other techniques can be used to facilitate engagement between a driver and a suture, and to allow free passage of one or more sutures therebetween.

The particular quantity of sutures used with a suture anchor and driver can depend on the size of the suture anchor and the driver, and in particular on the diameter of the inner lumen of the suture anchor and the size of the suture-engaging groove formed in the driver (for driver 60)

or the diameter of the lumen in the driver (for driver 70). For example, where the suture anchor has a relatively small inner lumen, the driver will necessarily have a relatively small diameter and thus small suture-engaging grooves (for driver 60) or a small inner lumen (for driver 70). It may therefore only be possible to use a single suture that is positioned around the suture-engaging member on the suture anchor, and that has two trailing ends extending through the suture-receiving grooves in the driver (for driver 60) or through the inner lumen in the driver (for driver 70). While a single suture can be sufficient to anchor tissue to bone, it is preferred to use more than one, and more preferably two or three sutures. Thus, rather than increasing a size of the suture anchor and/or the driver, the present invention provides various exemplary techniques for utilizing two sutures with a suture anchor and driver that are configured to seat only one suture. This is particularly advantageous as the suture anchor can be sized to be fully disposed within cortical bone, while the diameter of the inner lumen of the suture anchor and of the distal tip of the driver are maximized to increase the torque failure rating. This also enables the anchor to be made from a broad range of materials, including brittle or weaker materials such as those previously disclosed herein.

The present invention also provides exemplary methods for anchoring tissue to bone. While a method is described in connection with attaching soft tissue to bone, the methods and devices disclosed herein can be used in a variety of medical procedures for anchoring one structure to another. In general, a bore is formed in bone of a patient. The diameter of the bore is preferably slightly less than the largest outer diameter of the suture anchor, and the length of the bore is preferably the same as or slightly greater than a length of the suture anchor. The bore will extend fully through the cortical bone to allow the suture anchor to be fully engaged through the thickness of the cortical bone. The bore can also extend into the cancellous bone depending on the length of the suture anchor. One or more sutures can be coupled to the suture anchor using various techniques, including those disclosed in the aforementioned commonly-owned applications, and the distal tip of a driver can be inserted into the lumen in the suture anchor, for example as shown in FIG. 7. The trailing ends of the suture(s) can extend externally along the driver or they can extend through an inner lumen of the driver. The driver can then be used to insert the suture anchor into the bone tunnel. For example, where the suture anchor includes threads formed thereon, the driver can be rotated to thread the suture anchor into the bone hole. The threads will engage the bone hole thereby preventing removal of the suture anchor. Where the suture anchor includes dual threads, the second thread will provide additional fixation within the bone. By way of non-limiting example, FIG. 8 illustrates the suture anchor 10 of FIGS. 1A-1C implanted in bone B, and having three sutures 80a, 80b, 80c coupled thereto. As shown, the sutures 80a-80c extend around the suture-engaging member 14 and they extend through the lumen of the anchor 10 and through a lumen in the driver 70, thus allowing the driver 70 to drive the suture 10 into bone without interference from the sutures 80a-80c. In other embodiments, the driver can be used to tap the bone anchor into the bone hole, and an interference fit, compression fit, and/or surface features, such as ribs or protrusions, formed on the suture anchor can be used to retain the suture anchor within the bone hole. The driver can also optionally be used to impact a threaded suture anchor into the bone hole. The threads can allow for later removal of the suture anchor.

Once the bone anchor is properly anchored within the bone hole, various materials, such as those previously discussed herein, can be introduced through the driver and into or around the suture anchor. The driver can be removed, and the trailing ends of the suture(s) can then be used to anchor soft tissue to the bone. For example, one or both trailing ends of the suture(s) can be attached to a needle to allow the needle to be used to thread the suture through tissue to be anchor to the bone. The suture(s) can be threaded through tissue either prior to or after insertion of the suture anchor into bone. Once the soft tissue is approximated toward the bone, the trailing ends of the suture(s) can be secured together and the excess trimmed as is typical in these situations to complete the surgery. Once implanted, the cut-out extending into the inner lumen can allow materials, such as bone-growth promoting materials, sealants, adhesives, etc., to be introduced therein to facilitate fixation.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:
1. A suture anchor, comprising:
a body configured to be implanted in a patient, the body including:
a proximal portion with first and second threads on an external surface thereof, the proximal portion having an open proximal end configured to receive a driver therein,
a distal portion with an external surface having the first thread but not the second thread thereon, the distal portion having a closed, pointed distal tip, and
a suture-engaging member located entirely in the distal portion;
wherein the first and second threads extend over an entire length of the proximal portion, and the first thread extends over an entire length of the distal portion.
2. The suture anchor of claim 1, wherein an opening is formed through a sidewall of the body and is located entirely in the distal portion.
3. The suture anchor of claim 2, wherein a constant diameter portion extends along a partial longitudinal length of the suture anchor, and the opening is located entirely in the constant diameter portion proximal to the distal tip.
4. The suture anchor of claim 3, wherein the constant diameter portion is located partially in the distal portion of the body.
5. The suture anchor of claim 3, wherein the distal portion of the body includes part of the constant diameter portion and includes a non-constant diameter portion in which the distal tip is located.
6. The suture anchor of claim 1, wherein the suture-engaging member is configured to receive a suture therearound with trailing ends of the suture extending out of the open proximal end of the proximal portion of the body.
7. A suture anchor system, comprising:
the suture anchor of claim 1; and
the driver, the driver being configured to be inserted into the open proximal end of the proximal portion of the body and rotated to drive the body into bone with the first and second threads threading into the bone.

* * * * *